(12) United States Patent
Fedouloff et al.

(10) Patent No.: US 6,331,631 B1
(45) Date of Patent: Dec. 18, 2001

(54) PREPARATION OF 1-BUTYL-4-PIPERIDINYLMETHYLAMINE

(75) Inventors: Michael Fedouloff, Acton; David William Guest, Harlow; Gillian Elizabeth Smith, Bishops Stortford, all of (GB)

(73) Assignee: SmithKline Corporation p.l.c., Brentford (GB)

( * ) Notice: Subject to any disclaimer, the term of this patent is extended or adjusted under 35 U.S.C. 154(b) by 0 days.

(21) Appl. No.: 09/643,644

(22) Filed: Aug. 22, 2000

Related U.S. Application Data

(63) Continuation of application No. 09/254,513, filed as application No. PCT/EP97/05167 on Sep. 9, 1997.

(30) Foreign Application Priority Data

Sep. 11, 1996 (GB) .................................................. 9618967

(51) Int. Cl.[7] ........................ C07D 211/26; C07D 498/04
(52) U.S. Cl. ........................................... 546/201; 546/205
(58) Field of Search ...................................... 546/201, 245

(56) References Cited

FOREIGN PATENT DOCUMENTS

| 0 829 474 | 3/1998 | (EP) . |
|---|---|---|
| WO 93/05038 | 3/1993 | (WO) . |
| 93/05038 * | 3/1993 | (WO) . |
| WO 93/18036 | 9/1993 | (WO) . |
| 93/18036 * | 9/1993 | (WO) . |
| WO 94/08965 | 4/1994 | (WO) . |
| WO 96/38420 | 5/1996 | (WO) . |

OTHER PUBLICATIONS

B. Gutkowska and M. Krawczynska, *Roczniki Chemii*, 1976, 50(10), pp. 1791–1794.

* cited by examiner

*Primary Examiner*—Mukund J. Shah
*Assistant Examiner*—Hong Liu
(74) *Attorney, Agent, or Firm*—Soma G. Simon; William T. King; Charles M. Kinzig

(57) ABSTRACT

A process for the preparation of 1-butyl-4-piperidinylmethylamine using toluene as a solvent is disclosed.

5 Claims, No Drawings

PREPARATION OF 1-BUTYL-4-PIPERIDINYLMETHYLAMINE

This Application is a continuation of Ser. No. 09/254,513 filed Mar. 9, 1999, which is a 371 of PCT/EP97/05167 filed Dec. 9, 1996.

This invention relates to a new synthetic process to an intermediate which is useful for the preparation of compounds having pharmacological activity.

WO 93/03725, WO 93/05038, WO 93/08187, WO 93/16072, WO 93/18027, WO 93/18036, WO 94/07859, WO 94/08965, WO 94/08994, WO 94/08995, WO 94/08998, WO 94/17071 (SmithKline Beecham plc) describe compounds having 5-HT$_4$ receptor antagonist activity.

WO 93/18036, Example 3 describes N-[(1-$^n$butyl-4-piperidyl)methyl]-3,4-dihydro-2H-[1,3]oxazino[3,2-a]indole-10-carboxamide SB 207266, (the hydrochloride salt is SB 207266-A) which is being developed by SmithKline Beecham plc as the active ingredient in a medicament for treatment of irritable bowel syndrome.

WO 93/18036 describes a method of preparation of SB 207266-A from N-[(1-$^n$butyl-4-piperidyl)methyl]indole-3-carboxamide (i.e. the compound corresponding to SB 207266, without the oxazino moiety), by reacting with N-chlorosuccinimide and 3-bromo-1-propanol, followed by treatment with sodium carbonate. N-[(1-$^n$butyl-4-piperidyl)methyl]indole-3-carboxamide is prepared by coupling 1-butyl-4-piperidinylmethylamine with indole-3-carboxylic acid. The 1-butyl-4-piperidinylmethylamine is prepared as in Description 7 of WO 93/05038 and Description 1 of WO 93/18036, in a three stage process from isonipecotamide and 1-bromobutane, by alkylation in ethanol, to give the N-butyl derivative of isonipecotamide which is dehydrated to the corresponding nitrile and then reduced with LiAlH$_4$ in ether.

An alternative process for preparing 1-butyl-4-piperidinylmethylamine has now been discovered which involves the use of a common solvent, allowing the two stages to be run without isolation of the N-butyl derivative of isonipecotamide.

Accordingly, the present invention provides a process for the preparation of 1-butyl-4-piperidinylmethylamine, which process comprises:
  i) the reaction of 4-piperidinecarboxamide ("isonipecotamide") and 1-bromobutane to give the N-butyl derivative of isonipecotamide; followed by
  ii) reduction with LiAlH$_4$, characterised in that the reactions i) and ii) are carried out in toluene as solvent.

The advantages of this process as compared with that previously described are as follows:
  1. Toluene does not contain any additives, whereas THF contains a stabiliser (di-t-butylcresol) which can only be removed from 1-butyl-4-piperidinylmethylamine by fractional distillation.
  2. The overall process does not involve the preparation/isolation of the intermediate nitrile, and is therefore one step shorter.
  3. The process does not involve the isolation of the N-butyl derivative of isonipecotamide.
  4. The process uses a single solvent and eliminates the use of ethanol, chloroform and THF.
  5. the special extractive work-up of the LiAlH$_4$ reaction reduces the usage of solvent and loss of product on solid alumina residues.

The following Examples illustrate the invention.

EXAMPLE 1

4-Piperidinecarboxamide (iso-nipecotamide) and potassium carbonate (2 equivs.) were stirred in toluene and treated with 1-bromobutane (1 equiv.). The reaction mixture was heated at reflux (107–110° C.) for 2 hours. After cooling to 80–85° C. the mixture was washed with hot water followed by hot aqueous potassium carbonate solution. The resulting toluene solution of 1-butyl-iso-nipecotamide was dried by azeotropic distillation, maintaining the reaction volume by addition of fresh toluene.

The toluene solution was cooled to 0–5° C., under nitrogen. A solution of LiAlH$_4$.2 THF in toluene (1.0 molar solution; 2.0 equivs.) was added over 1 hour, keeping the temperature <10° C. The mixture was allowed to warm to room temperature and was then heated to reflux for 1 h our. After cooling to 0–5° C., 32% w/w sodium hydroxide solution (1.5 equivs. wrt substrate) was added cautiously over 1 hour, keeping the temperature <10° C. The mixture was stirred for 30 minutes at ambient temperature and the precipitate filtered through celite, washing the bed thoroughly with toluene. The filtrate was evaporated in vacuo to give 1-butyl-4-piperidinylmethylamine as a pale yellow oil, containing ~13% by weight toluene, in 72% yield (after adjusting for toluene content).

EXAMPLE 2

Alternatively the first part of the preparation may be carried out as follows:

4-Piperidinecarboxamide (iso-nipecotamide) and 5M aqueous potassium carbonate solution (2 equivs.) were stirred in toluene and treated with 1-bromobutane (1 equiv.). The reaction mixture was heated at reflux (107–110° C.) for 2 hours. After cooling to 70–80° C. the mixture was washed with hot water followed by hot aqueous potassium carbonate solution. The resulting toluene solution of 1-butyl-iso-nipecotamide was dried by azeotropic distillation, maintaining the reaction volume by addition of fresh toluene.

EXAMPLE 3

A 3 L vessel was purged with nitrogen and charged with iso-nipecotamide (112.1 g 0.87 mol) and dry toluene (78.5 ml). The suspension was warmed to 50° C. and potassium carbonate (248 g, 1.79 mol) and butyl bromide (119.8 g, 0.87 mol) were added in one portion. The resulting mixture was heated at reflux under Dean-Stark conditions for three hours and then cooled to 65° C. and quenched by addition of water (875 ml). The aqueous phase was separated at about 80° C. and the organic layer dried by azeotropic distillation of toluene (200 ml). Fresh toluene (200 ml) was added to maintain a constant volume.

The reaction mixture was cooled to about 5° C. and treated, dropwise, with a solution of lithium aluminium hydride.2THF in toluene (500 ml, 3.5M, 1.75 mol). The mixture was stirred at ambient temperature for one hour and then at about 55° C. for a further two hours. The reaction was then quenched by cautious addition of sodium hydroxide solution (1200 ml, 10.8M) and heated to about 70° C. The aqueous phase was separated and washed twice with toluene (300 ml each wash). The combined organic washes were concentrated under reduced pressure and the product 1-butyl-4-piperidinylmethylamine (SB-211156) (127 g) was isolated as a pale yellow oil in 85% yield by vacuum distillation (bp 106° C. at 20 mm Hg approx.).

What is claimed is:
1. A process for the preparation of 1-butyl-4-piperidinylmethylamine, which process comprises:
  i) the reaction of 4-piperidinecarboxamide and 1-bromobutane to give the N-butyl derivative of 4-piperidinecarboxamide followed by ii) reduction with LiAlH$_4$, characterised in that the reactions i) and ii) are carried out in toluene as solvent.

2. A process according to claim 1 in which the reaction mixture after the reduction is treated with hot sodium hydroxide solution and the mixture is extracted with an organic solvent.

3. A process according to claim 1 wherein the process is run without isolation of the N-butyl derivative of 4-piperidinecarboxamide.

4. A process according to claim 1 wherein in reaction (i) potassium carbonate is added and the mixture is heated at reflux under Dean-Stark conditions.

5. A process for the preparation of N-[(1-"butyl-4-piperidyl)methyl]-3,4-dihydro-2H-[1,3]oxazino[3,2-a]indole-10-carboxamide, or a pharmaceutically acceptable salt thereof, which process comprises preparing 1-butyl-4-piperidinylmethylamine according to the process of claim 1, followed by coupling with a derivative of the carboxylic acid function of an indole-3-carboxylic acid, and, thereafter, as necessary converting the indole and/or substituents, including cyclisation to 3,4-dihydro-2H-[1,3]oxazino[3,2-a] indole.

* * * * *

UNITED STATES PATENT AND TRADEMARK OFFICE
CERTIFICATE OF CORRECTION

PATENT NO.    : 6,331,631 B1
DATED         : December 18, 2001
INVENTOR(S)   : Michael Fedouloff, David William Guest and Gillian Elizabeth Smith It is certified that error appears in the above-identified patent and that said Letters Patent is hereby corrected as shown below:

<u>Title page,</u>
Item [75], Inventors, "Michael Fedouloff, David William Guest, Gillian Elizabeth Smith", should be:
-- Michael Fedouloff, David William Guest, Gillian Elizabeth Smith, John Bryce Strachan --
Item [73], Assignee, "SmithKline Corporation p.l.c.," should be
-- SmithKline Beecham p.l.c. --

Signed and Sealed this

Fifth Day of August, 2003

JAMES E. ROGAN
*Director of the United States Patent and Trademark Office*